US009610039B2

(12) United States Patent
Golosarsky et al.

(10) Patent No.: US 9,610,039 B2
(45) Date of Patent: Apr. 4, 2017

(54) HAND-HELD NEUROSCREENING DEVICE

(71) Applicants: Boris Golosarsky, Hollis, NH (US); James Bernhard, Plainville, MA (US); Michael Brown, Nashua, NH (US); Craig E. Norton, Hudson, NH (US); Matthew G. Rouleau, Goffstown, NH (US)

(72) Inventors: Boris Golosarsky, Hollis, NH (US); James Bernhard, Plainville, MA (US); Michael Brown, Nashua, NH (US); Craig E. Norton, Hudson, NH (US); Matthew G. Rouleau, Goffstown, NH (US)

(73) Assignee: Prosenex, LLC, Hudson, NH (US)

( * ) Notice: Subject to any disclaimer, the term of this patent is extended or adjusted under 35 U.S.C. 154(b) by 232 days.

(21) Appl. No.: 14/061,786

(22) Filed: Oct. 24, 2013

(65) Prior Publication Data

US 2014/0155778 A1    Jun. 5, 2014

Related U.S. Application Data

(63) Continuation-in-part of application No. 13/054,136, filed as application No. PCT/US2009/004159 on Jul. 17, 2009, now Pat. No. 8,579,830.

(Continued)

(51) Int. Cl.
*A61B 19/00* (2006.01)
*A61B 5/00* (2006.01)
*A61F 7/00* (2006.01)

(52) U.S. Cl.
CPC ............ *A61B 5/483* (2013.01); *A61B 5/0051* (2013.01); *A61B 5/4827* (2013.01); *A61B 5/441* (2013.01);

(Continued)

(58) Field of Classification Search
CPC ..... A61B 5/0051; A61B 5/483; A61B 5/4827; A61B 5/4824; A61F 7/00; A61F 7/007; A61F 2007/0087
See application file for complete search history.

(56) References Cited

U.S. PATENT DOCUMENTS 4,653,507 A    3/1987  Laudadio
5,002,065 A    3/1991  LaCourse et al.
(Continued)

FOREIGN PATENT DOCUMENTS

EP    0136881    4/1985
EP    0569920    11/1993
(Continued)

OTHER PUBLICATIONS

Bertelsmann, F.W. et al., "Thermal discrimination thresholds in normal subjects and in patients with diabetic neuropathy", Journal of Neurology, Neurosurgery, and Psychiatry, 1985, pp. 686-690.

(Continued)

*Primary Examiner* — Devin Henson
(74) *Attorney, Agent, or Firm* — Joseph E. Maenner; Maenner & Associates, LLC

(57) ABSTRACT

A hand-held neuroscreening device includes an elongate handle having a first end, a second end, and longitudinal axis extending therethrough between the first end and the second end. A head portion is fixedly attached to the first end of the handle. The head portion has a longitudinal axis, a fixed temperature surface extending in a first plane oblique to the head portion longitudinal axis, and a variable temperature surface extending in a second plane oblique to the first plane. A method of using the device is also disclosed.

18 Claims, 15 Drawing Sheets

Related U.S. Application Data

(60) Provisional application No. 61/081,536, filed on Jul. 17, 2008.

(52) U.S. Cl.
CPC ............ *A61B 5/4824* (2013.01); *A61B 5/742* (2013.01); *A61F 7/00* (2013.01); *A61F 7/007* (2013.01); *A61F 2007/0087* (2013.01)

(56) References Cited

U.S. PATENT DOCUMENTS

| | | | |
|---|---|---|---|
| 5,209,227 A * | 5/1993 | Deutsch | F25B 21/04 607/104 |
| 5,363,859 A | 11/1994 | Tuckett et al. | |
| 5,373,853 A * | 12/1994 | Assal | A61B 5/483 600/555 |
| 5,381,805 A * | 1/1995 | Tuckett | A61B 5/0051 600/552 |
| 5,823,969 A | 10/1998 | Christy | |
| 7,854,703 B2 | 12/2010 | Poisner | |
| 2005/0075669 A1* | 4/2005 | King | A61N 1/36021 607/2 |
| 2007/0191730 A1 | 8/2007 | Speidel | |
| 2009/0227890 A1 | 9/2009 | Lanfermann et al. | |
| 2012/0109003 A1* | 5/2012 | Ordriozola Orlandi | A61B 5/4827 600/552 |

FOREIGN PATENT DOCUMENTS

| | | |
|---|---|---|
| EP | 136881 | 4/2014 |
| JP | 62-12310 | 1/1987 |
| JP | 2005052598 | 3/2005 |
| WO | WO87/07969 | 12/1987 |
| WO | WO00/59377 | 10/2000 |

OTHER PUBLICATIONS

European Search Report for EP application 09798324.1, Dec. 12, 2012.
Written Opinion and International Preliminary Report on Patentability for PCT application No. PCT/US2009/004159, Jan. 18, 2011.
Website printout for www.usneurologicals.com, Jul. 4, 2007, 17 pages.
Office Action dated Aug. 30, 2011 for U.S. Appl. No. 13/054,136.
Final Office Action dated Feb. 2, 2012 for U.S. Appl. No. 13/054,136.
EPO Communication for EP09798324.1-1657/2312999, mailed Jan. 19, 2015, 2 pages.
EPO Communication for EP09798324.1-1657/2312999, mailed Jan. 15, 2015, 5 pages.

* cited by examiner

HAND-HELD NEUROSCREENING DEVICE

CROSS-REFERENCE TO RELATED APPLICATIONS

The present application is a Continuation-in-Part application of U.S. patent application Ser. No. 13/054,136, filed on Jan. 14, 2011, which is a 371 of PCT Application PCT/US2009/004159, filed on Jul. 17, 2009, which claims priority from U.S. Provisional Patent Application Ser. No. 61/081,536, filed on Jul. 17, 2008, all of which are incorporated by reference in their entireties.

BACKGROUND OF THE INVENTION

Neuropathy is a medical condition where a patient has reduced sensitivity in through-the-skin sensing of temperature variations, vibrations, and tactile stimulation. Neuropathy is common for patients with diabetes. Attention to diabetes has increased significantly as more individuals are being diagnosed with some form of the disease. Early and accurate diagnosis of neuropathies associated with diabetes or other medical issues may lead to earlier treatment to reduce the effect of these issues on the patient.

SUMMARY OF THE INVENTION

Briefly, the present invention provides a hand-held neuroscreening device comprising an elongate handle having a first end, a second end, and longitudinal axis extending therethrough between the first end and the second end. A head portion is fixedly attached to the first end of the handle. The head portion has a longitudinal axis, a fixed temperature surface extending in a first plane oblique to the head portion longitudinal axis, and a variable temperature surface extending in a second plane oblique to the first plane.

Further, the present invention provides a method of using the above-described device to screen for neuropathy in a patient. The method includes selecting between operating the fixed and variable temperature surfaces and the vibration probe; touching a location on a patient with the device; determining whether the patient is able to discriminate between temperature differences between the fixed temperature pad and the variable temperature pad if the step of operating the fixed and variable temperature surfaces was selected; and determining whether the patient is able to discriminate vibrations if the step of operating the vibration probe was selected.

The present invention also provides a method of screening for neuropathy in a patient, the method comprising the steps of: (a) using a single hand-held device, touching the patient in a location with a first temperature pad, the first temperature pad being electronically held at a fixed temperature; (b) using the single hand-held device, touching the patient in the location with a second temperature pad, the second temperature pad being held electronically at a variable temperature, the variable temperature being different than the fixed temperature by a delta temperature; and (c) determining whether the patient can distinguish between the fixed temperature and the variable temperature and, if the patient cannot distinguish between the fixed temperature and the variable temperature, increasing the delta temperature and repeating steps (a)-(c) until the patient can distinguish between the fixed temperature and the variable temperature.

The present invention also provides a hand-held neuroscreening device, comprising a handle portion containing a controller, a head portion extending from the handle portion. The head portion comprises a fixed temperature surface operatively coupled to the controller, a variable temperature surface operatively coupled to the controller; and a vibration surface extending outwardly from the head portion, the vibration surface being operatively coupled to the controller.

Further, the present invention also provides a hand-held neuroscreening device comprising a generally elongate handle portion. The handle portion contains an electronic controller located inside the handle portion and a plurality of control buttons operatively connected to the electronic controller. The plurality consists of a power button, a temperature selection button, a vibrator selection button, an up button, and a down button. A head portion is connected to an end of the handle portion. The head portion contains a fixed temperature surface operatively coupled to the controller. The fixed temperature surface is connected to a first heat sink. A variable temperature surface is operatively coupled to the controller. The variable temperature surface is connected to a second heat sink. A vibration surface extends outwardly from the head portion. The vibration surface is operatively coupled to the controller. A fan is configured to blow air over the first and second heat sinks.

BRIEF DESCRIPTION OF THE DRAWINGS

The foregoing summary, as well as the following detailed description of exemplary embodiments of the invention, will be better understood when read in conjunction with the appended drawings, which are incorporated herein and constitute part of this specification. For the purposes of illustrating the invention, there are shown in the drawings exemplary embodiments of the present invention. It should be understood, however, that the invention is not limited to the precise arrangements and instrumentalities shown. In the drawings, the same reference numerals are employed for designating the same elements throughout the several figures. In the drawings.

DETAILED DESCRIPTION OF THE INVENTION

Figure 1:
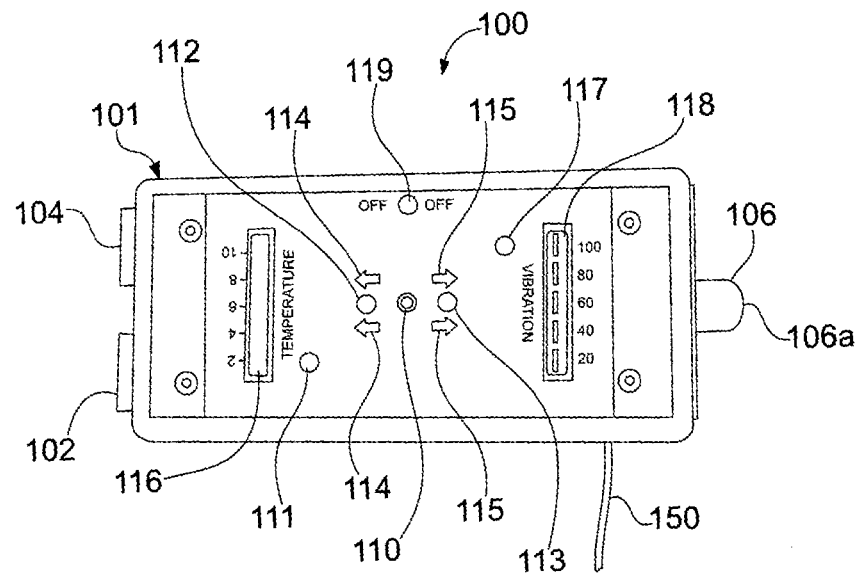
FIG. 1 is a top plan view of a neuropathy detection device according to an exemplary embodiment of the present invention.

Although the invention is illustrated and described herein with reference to specific embodiments, the invention is not intended to be limited to the details shown. Rather, various modifications may be made in the details within the scope and range of equivalents of the disclosure without departing from the invention. The invention is best understood from the following detailed description when read in connection with the accompanying drawing figures, which show exemplary embodiments of the invention selected for illustrative purposes. The invention will be illustrated with reference to the figures. Such figures are intended to be illustrative rather than limiting and are included herewith to facilitate the explanation of the present invention.

Referring to FIGS. 1-4 in general, a hand-held neuro-screening device 100 ("device 100") that is used to screen for neuropathy in patients according to a first exemplary embodiment of the present invention is shown. Neuropathy is common for patients with medical issues, such as diabetes or erectile dysfunction. Device 100 includes a body 101 having an exposed neutral temperature surface 102 and an exposed variable temperature surface 104 at one end of body 101, and an exposed vibration surface 106 that extends outwardly from an opposing end of body 101. A filament 108 extends outwardly from body 101. Filament 108 may be a monofilament, such as nylon wire.

A medical professional, such as, for example, a physician, may use device 100 on a patient by touching various locations on the patient's skin with surfaces 102, 104, 106 and/or filament 108. The patient's reaction to these touches may give the physician an indication of a level of neuropathy in the patient, which may in turn aid or enable the physician to diagnose the patient.

Figure 4:
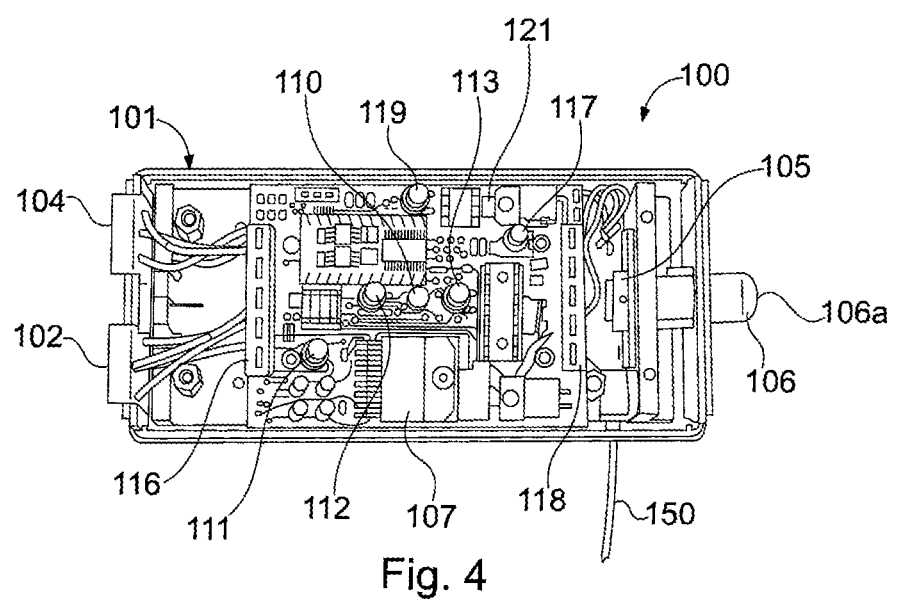
FIG. 4 is a top plan view of the neuropathy detection device of FIG. 1, with the top cover removed.
Figure 5:
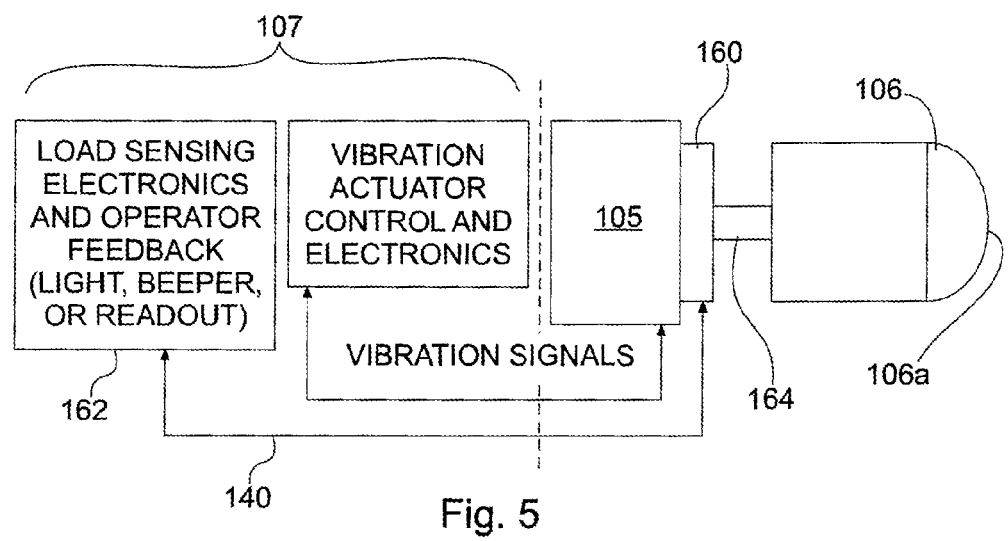
FIG. 5 is a schematic drawing of an exemplary embodiment of a force sensor for a vibrating end effector in the neuropathy detection device of FIG. 1.

Two separate modes of operation are provided for device 100: temperature (using surfaces 102, 104) and vibration (using surface 106), as well as a tactile test (using filament 108). Each mode can be utilized at any time and the operator may switch back and forth between the two modes and/or the tactile test. Controls and indicators are included on body 101 to allow the operator to control surfaces 102, 104, 106 and to give the operator an indication of the operating parameters of surfaces 102, 104, 106. A controller, such as a microcontroller 107, shown in FIGS. 4 and 5, is used to control operation of surfaces 102, 104, 106.

Figure 2:
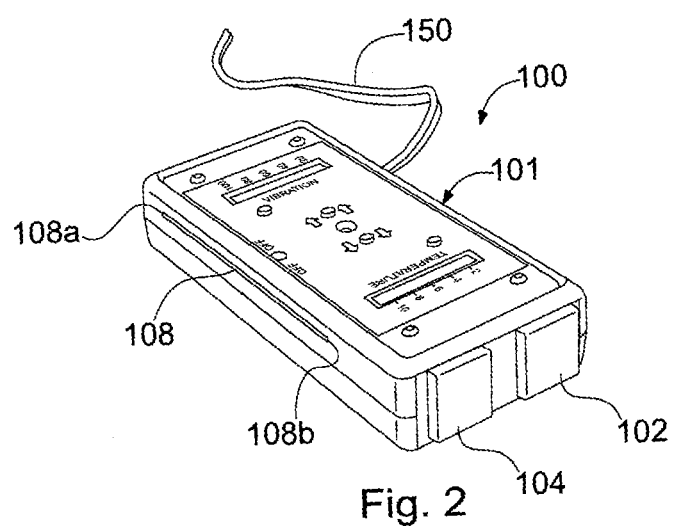
FIG. 2 is a front perspective view of the neuropathy detection device of FIG. 1.

The patient's ability to discern the differences between the temperatures of neutral temperature surface 102 and variable temperature surface 104, positioned at various locations on the patient's skin, gives the physician an indication of the level of neuropathy. Referring specifically to FIGS. 1, 2, and 4, in an exemplary embodiment, neutral temperature surface 102 and variable temperature surface 104 are both generally square, flat pads with sides that are about 1½ to 2 cm long.

Variable temperature surface 104 may be independently controlled by the operator such that the temperature difference between neutral temperature surface 102 and variable temperature surface 104 varies up to about 10 degrees Celsius. In an exemplary embodiment, neutral temperature surface 102 may be set by controller 107 at about 25 degrees Celsius. Variable temperature surface 104 may be varied at 2 degree increments between a temperature of between about 15 and about 25 degrees Celsius. While in this exemplary embodiment, the temperature of variable temperature surface 104 may be set to be lower than the temperature of neutral temperature surface 102, those skilled in the art will recognize that the temperature of variable surface 104 may be set higher than the temperature of neutral temperature surface 102.

A power indicator LED 110 illuminates when power is provided to device 100. A temperature mode button 111 may be pressed to activate the temperature mode and to provide power to heat surfaces 102, 104. Neutral temperature surface 102 is powered to a fixed temperature, such as, for example, 25 degrees Celsius, and variable temperature surface 104 at a variable temperature in degree increments, such as, for example, increments of 2 degrees Celsius. The operator can control the temperature of variable temperature surface 104 by using increment buttons 112, 113. Arrows 114 on either side of increment button 112 pointing toward surfaces 102, 104 indicate that the operation of increment button 112 raises the temperature difference between neutral temperature surface 102 and variable surface 104, while arrows 115 on either side of increment button 113 pointing away from surfaces 102, 104 indicate that the operation of increment button 113 lowers the temperature difference between neutral temperature surface 102 and variable surface 104. An LED bar graph 116 displays a temperature offset between neutral temperature surface 102 and variable temperature surface 104. An "Off" button 119 turns off device 100.

Temperature variations on surfaces 102, 104 are created through standard solid state thermoelectric devices known as "Peltier Devices." As shown in FIG. 5, a Peltier Device 120 labeled "Steady Peltier" controls neutral temperature surface 102 (shown in FIG. 1), while a Peltier Device 122 labeled "Variable Peltier" controls variable temperature surface 104 (shown in FIG. 1).

A Peltier Device is essentially a solid state heat pump with no moving parts. A DC voltage is applied to the device, which causes heat to move from one side to the other. This movement of the heat causes an apparent cooling of one side and heating of the other side. Exemplary Peltier Devices used for surfaces 102, 104 may be about 1.25 cm square and about 0.25 cm thick. The direction of heat flow within a Peltier Device can be reversed by simply reversing the polarity of the DC current applied to the device. By constructively controlling the current level and polarity of the current applied to a Peltier Device, a constant temperature can be maintained.

Peltier Devices 120, 122 used in the exemplary embodiment of device 100 may be identical. Each Peltier Device 120, 122 is powered by a separate dual H Bridge 124, 126, respectively. An H bridge has two outputs that can have its output commanded to reverse polarity. An H bridge is either "on" or "off," meaning that the H bridge either delivers full power to the Peltier, or no power. Since it is necessary to set various heat pump levels (and therefore temperature as measured on surfaces 102, 104), controller 107 varies the electrical current levels to H bridges 124, 126. This may be done via pulse width modulation (PWM) which provides a repeated signal of "on" and then "off." The relative time of "off" versus "on" will set, on average, the power going to each Peltier Device 120, 122 and therefore the temperature at surfaces 102, 104, respectively.

Each surface 102, 104 includes a respective temperature sensor 128, 130, which provides feedback to microcontroller 107 via a respective analog to digital (A/D) converter 132, 134.

Figure 3:
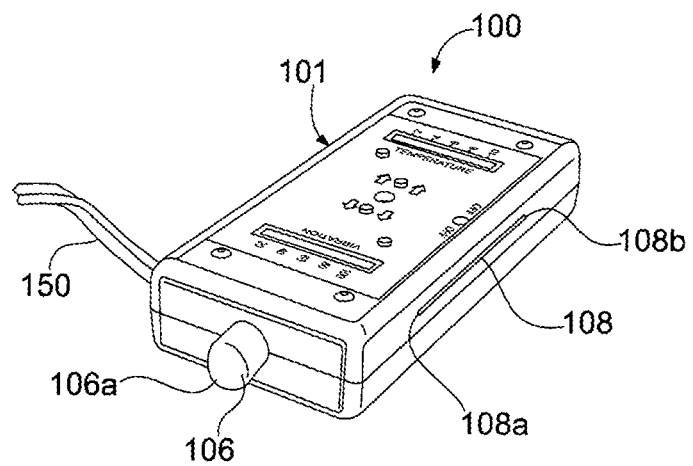
FIG. 3 is a rear perspective view of the neuropathy detection device of FIG. 1.

The patient's ability to discern vibrations at various locations on the patient's skin also gives the physician an indication of the level of neuropathy. Referring specifically to FIGS. 1, 3, and 4, vibration surface 106 may extend outwardly from body 101 and have a generally cylindrical shape with a hemispherical end. Vibration surface 106 may be controlled to vibrate in and out at constant frequency, but with a variable amplitude. In an exemplary embodiment, vibration surface 106 vibrates at a frequency of about 120 Hz, although other frequencies are also contemplated. The amplitude of vibration of vibration surface 106 may be varied between about 100 percent of full amplitude and about 20 percent of full amplitude. An LED bar graph 118 displays a percentage of vibration amplitude relative to a maximum available amplitude. In an exemplary embodiment, the amplitude may be adjusted in 20 percent increments (100, 80, 60, 40, or 20 percent of full amplitude), although those skilled in the art will recognize that other increments may be used.

As illustrated in FIG. 5, in an exemplary embodiment, vibration for vibrating surface 106 may be provided by a magnetic coil moving a magnet (shown collectively as magnet 105). The magnet 105 may be coupled to vibrating surface 106. A signal from microcontroller 107 to the coil is a constant frequency. A low power signal from microcontroller 107 may be amplified using a simple operational amplifier 136 (shown schematically in FIG. 6) and transistor (not shown). The amplitude of the vibration is also controlled by microcontroller 107. While an exemplary mechanism for vibrating the vibrating surface 106 is shown, those skilled in the art will recognize that other mechanisms may be used.

Referring to FIGS. 1 and 4, increment buttons 112, 113 may be used to adjust the vibration amplitude down or up as desired. Increment button 113 will increase the vibration amplitude, while increment button 112 will decrease the vibration amplitude. "Off" button 119 turns off device 100.

Optionally, as illustrated in FIG. 5, vibration surface 106 may incorporate a pressure sensor 140. Pressure sensor 140 may include a load cell 160 that is electronically coupled to a load sensing electronics component 162 in controller 107 and generates an indication when sufficient pressure is applied by device 100 on the patient's skin. The indication may be an audible indication, such as, for example, a beep, a visual indication such as, for example, a light, or some other suitable type of indication to signify to the user that device 100 is being applied to the patient's skin with sufficient force to enable the patient to sense the vibrations from vibration surface 106. The indicator would operate as long as the pressure applied to the patient is sufficient to enable the patient to sense the vibrations.

Load cell 160 may be coupled to magnet 105 and disposed between magnet 105 and vibration surface 106. Optionally, as illustrated in FIG. 5, a mechanical extension 164 may couple load cell 160 to vibration surface 106.

Figure 6:
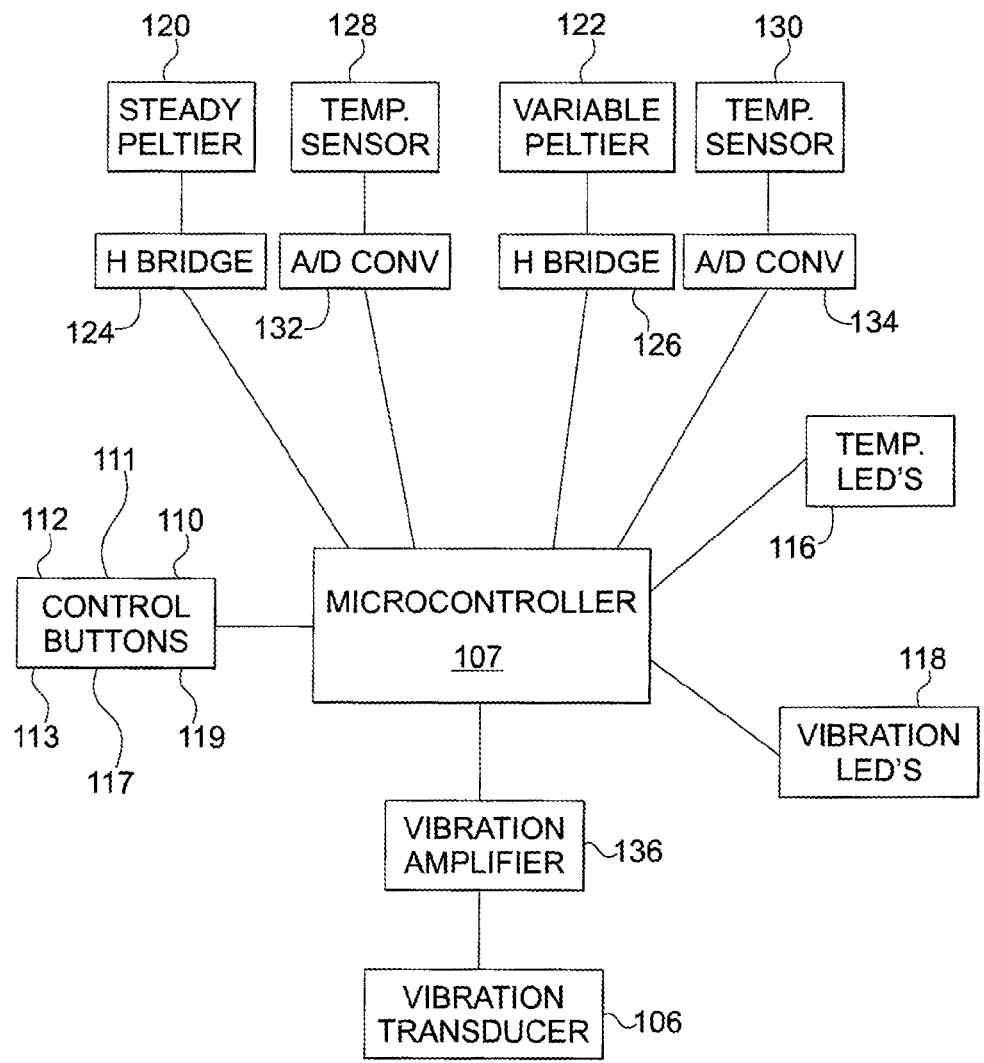
FIG. 6 is a block diagram illustrating a functional layout of a circuit used to operate the neuropathy detection device of FIG. 1.

Referring to the control diagram of FIG. 6, microcontroller 107 may be used to control the temperature of surfaces 102, 104 and the vibration of vibration surface 106. Microcontroller 107 is disposed within body 101 and may be an 8 bit industrial processor with 16 digital inputs and outputs. An associated printed circuit board 121 (shown in FIG. 4) not only contains the circuitry, but also provides the proper layout and mounting for LED's 116, 118 and buttons 110, 111, 112, 113, 117, 119.

Referring to FIGS. 2 and 3, filament 108 provides a touch sensation test. In an exemplary embodiment, the tactile aspect of device 100 utilizes a standard monofilament nylon wire for filament 108, having a free end 108a, which is used to check the patient's tactile sensitivity. For protection when not in use, filament 108 may be disposed against the outside of body 101 and can be readily pivoted about a pivoting end 108b by the operator at any time. Alternatively, although not shown, filament 108 may be housed within body 101 and pulled out from body 101 when desired. After use, filament 108 may be pushed back into body 101 for storage.

In an exemplary embodiment, device 100 may be powered by standard 110 volt alternating current, stepped down to 6 volt direct current through a transformer. Internally, a 5 volt regulator may be provided to provide voltage to digital components within device 100.

Electrical power may be provided to device 100 through an electrical cord 150, which is partially shown in FIGS. 1-4. Alternatively, device 100 may be powered by batteries (rechargeable or disposable) that are contained within body 101 of device 100.

While body 101 is illustrated in FIGS. 1-4 as a generally rectangular enclosure, those skilled in the art will recognize that body 101 may be other shapes as well, including, but not limited to, a cylindrically shaped body.

Device 100 may optionally be used to record data obtained during testing. In a first embodiment, device 100 has no storage capacity within itself, but transmits data from microcontroller 107 via radio frequency or other suitable transmission medium to a storage device, such as, for example, a personal/laptop computer. The patient's profile may have already been called up on the storage device and the data transmitted from device 100 is automatically transmitted to the patient's file. The information transmitted from device 100 may include maximum/minimum temperatures and or vibration amplitudes generated by device 100.

Alternatively, device 100 may have memory within microcontroller 107 or coupled to microcontroller 107 and the capability to receive/transmit information. Device 100 may receive patient information uploaded to device 100 from the personal/laptop computer. Device 100 may include an indicator, such as, for example, an LCD or LED screen that displays the patient information so that the operator knows that the correct patient information has been downloaded to device 100. Data obtained during operation of device 100 is then associated with the patient information. This data may be transmitted back to the personal/laptop computer instantly, after all data for the particular patient is obtained, or even after uses with several different patients, such as, for example, at the end of a work day. Those skilled in the art will recognize that known methods may be used to store and transmit data between device 100 and another device.

Further, if device 100 is battery operated with rechargeable batteries that are recharged by inserting device into a recharging station (not shown), the recharging station may include a port to engage device 100 for downloading data from device 100 into a storage device.

To operate device 100, the operator turns on device 100 by pressing either temperature mode button 111 or vibration mode button 117. The operator can press either mode button 111, 117 at any time to switch between temperature and vibration modes.

To conserve energy (and battery power, if batteries are used), device 100 times out after 30 seconds on its own if no buttons are pressed. Any adjustment using increment buttons 112, 113 adds a new period of 30 seconds to the timeout mechanism. The operator can add another 30 seconds by simply pressing the appropriate mode button 111, 117. "Off" button 119 may be pressed at any time to shut down device 100 prior to device 100 timing out.

When device 100 is first powered on, device 100 will default to make variable temperature surface 104 have a 2 degree offset from neutral temperature surface 102. At any time, the operator can use increment buttons 112, 113 to adjust this offset. LED bar graph 116 shows the operator which offset is currently being provided by device 100. There is a small delay in attaining the proper temperatures and LED bar graph 116 reflects this situation by blinking while surfaces 102, 104 are brought to their desired temperatures. LED bar graph 116 remains steadily lit when surfaces 102, 104 are at their desired temperature(s). The operator is free to adjust device 100 to any of the preprogrammed offsets based on his need for further tests as dictated by the patient's responses. Device 100 may be programmed to shut itself off if no buttons have been pushed for any desired time level, such as 60 seconds.

If the operator desires to operate the temperature mode first, the operator presses temperature mode button 111. Device 100 will begin to appropriately heat or cool both temperature surfaces 102, 104. Device 100 will always attempt to make neutral temperature surface 102 stay at 25 degrees Celsius. If no other action is taken by the operator, device 100 will attempt to make variable temperature pad 104 two (2) degrees below the temperature of neutral temperature surface 102. LED bar graph 116 will blink at "−2" while device 100 works to acquire the proper temperature, and will become steady when the proper temperatures on both surfaces 102, 104 (i.e., a temperature difference of 2 degrees Celsius between surfaces 102, 104) are reached. Increment buttons 112, 113 may be used to increase or decrease the temperature differential. With each change in desired offset, LED bar graph 116 moves to represent the new differential. The corresponding LED on LED bar graph 116 will blink while device 100 is working to achieve the new temperature goal and will remain steady when the proper temperatures have been reached.

When LED bar graph 116 is illuminating in steady state, the operator then applies surfaces 102, 104 simultaneously to an area on the patient's skin surface. The operator then asks for the patient's feedback depending on whether the patient could sense the temperature offset between surfaces 102, 104. This offset may first be set to the lowest amount (e.g., 2 degrees) and may then be incremented to larger offset values. In an exemplary embodiment, each increment makes variable surface 104 two (2) degrees cooler. Once the patient reports that he/she can feel the offset, the operator then knows the patient's temperature offset detection level for that particular part of the body.

In addition to temperature testing, the operator may also perform a vibration study. The operator presses vibration mode button 117, activating vibration mode, causing vibration surface 106 to vibrate at 120 Hz, and at 100% of the amplitude of vibrating surface 106. The operator may use increment buttons 112, 113 to adjust the vibration amplitude down or up as desired. Increment button 113 will increase the vibration amplitude, while increment button 112 will decrease the vibration amplitude. As noted earlier with respect to the temperature mode, device 100 shuts down after 30 seconds if no additional inputs are provided. Any adjustment to the amplitude via increment buttons 112, 113 will reset the 30 second clock.

The operator touches an end 106a of vibration surface 106 to the area of interest on the patient's body. Load cell 160 transmits a signal to load sensing electronics component 162, which transmits a signal (e.g., light, audible, etc.) to the operator to let the operator know that vibration surface 106 is engaging the patient with sufficient force. With vibration surface 106 vibrating, the patient may react by stating whether or not he/she can feel the vibration. The operator may then decrease the amplitude of the vibration and obtain further patient feedback to discern where the patient's threshold limit of detection may be. The operator can freely move vibration amplitude up and down as desired, with the changes in amplitude happening virtually instantaneously.

The operator may also perform a tactile study. Filament 108 may be moved away from body 101 by rotating filament 108 about pivoting end 108b to allow free end 108a of filament 108 to extend away from body 101. Free end 108a may be gently pressed into the skin of the patient to determine the patient's sensation of filament 108 being pressed into the skin.

While an operating sequence of temperature, vibration, and touch using device 100 is described above, those skilled in the art will recognize that device 100 may be used in any other appropriate order, and in any combination of tests.

Figure 7:
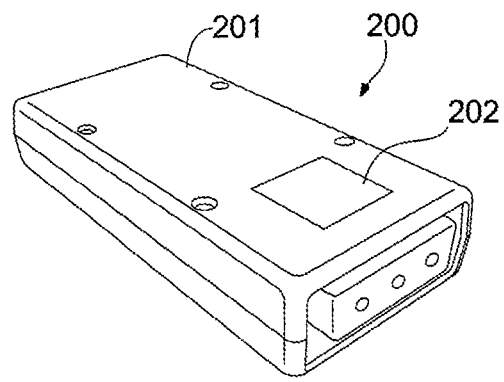
FIG. 7 is a top perspective view of a neuropathy detection device according to an alternative exemplary embodiment of the present invention.
Figure 8:
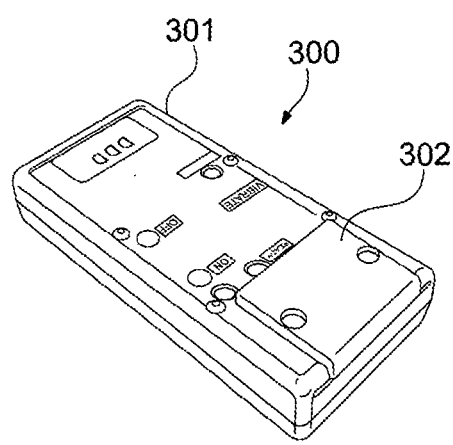
FIG. 8 is a top perspective view of a neuropathy detection device according to another alternative exemplary embodiment of the present invention.
Figure 9:
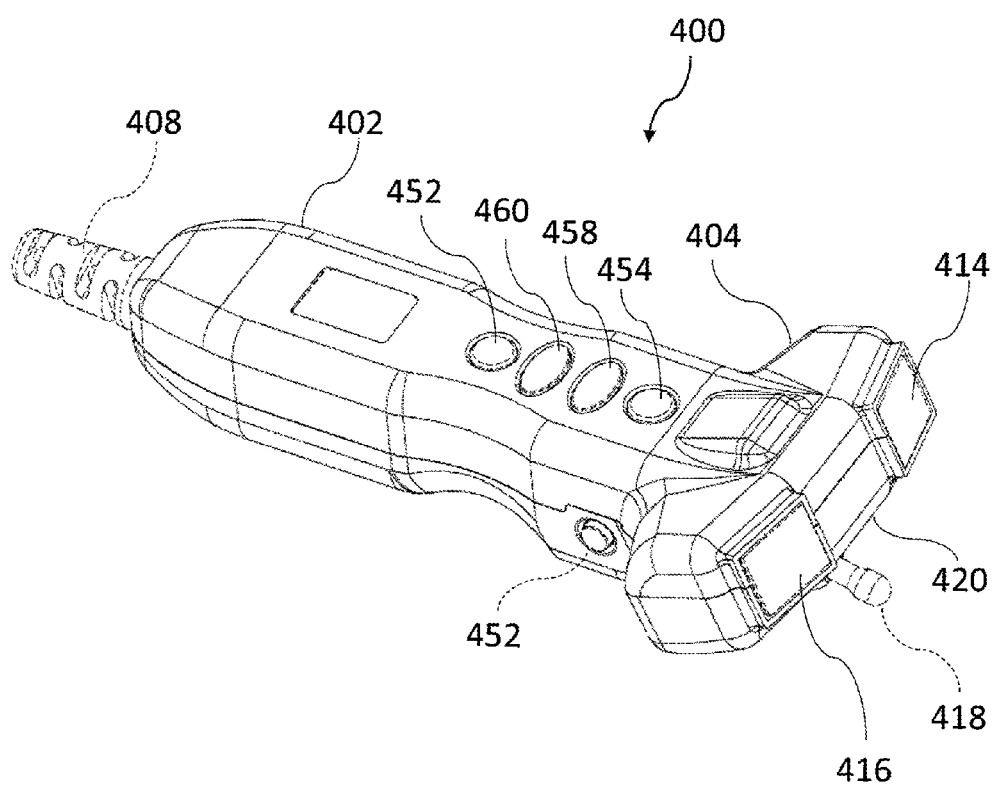
FIG. 9 is a perspective view of a neuropathy detection device according to a fourth exemplary embodiment of the present invention.

Alternative embodiments of hand-held devices 200, 300 according to the present invention are illustrated in FIGS. 7 and 8, respectively. Devices 200, 300 incorporate temperature surfaces on opposing sides of body 201, 301, respectively. In FIGS. 6 and 7, only neutral surfaces 202, 302 are shown, with variable temperature surfaces, not shown, being located on the underside of body 201, 301 respectively. In device 200, neutral surface 202 is flush with body 201, while in device 300, neutral surface 302 extends outwardly from body 301.

Still another alternative embodiment of a hand-held neuroscreening device 400 according to the present invention is shown in FIGS. 9-15. Device 400 includes a generally elongate handle portion 402 that extends along a longitudinal axis 403. Device 400 also includes a head portion 404 extending from a first end 406 of elongate handle portion 402 and an electrical supply cable connection 408 extending from a second end 410 of elongate handle portion 402. Cable connection 408 may be electrically connected to a power supply (not shown), such as an SL Power Electronics MENB1030A0503F01 PRZ, Part Number PMC-40008.

Head 404 extends generally along an axis 412 running generally perpendicular to the longitudinal axis 403. As shown FIG. 12, head 404 extends along a head axis 405 at an angle β of between about 20 degrees and about 30 degrees relative to longitudinal axis 403. Head 404 includes an end surface 420 that extends in a plane generally perpendicular to head axis 405.

Figure 11:
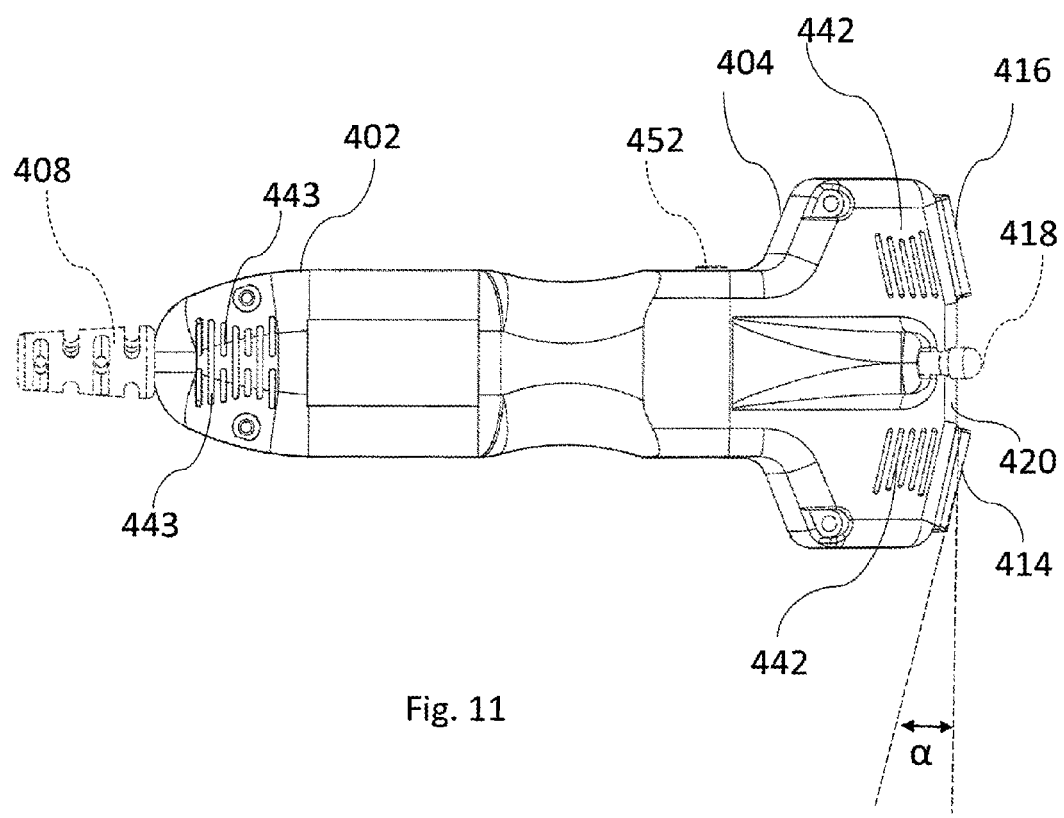
FIG. 11 is a bottom view of the neuropathy detection device of FIG. 9.

Head portion 404 includes a pair of temperature pads 414, 416 that are used to determine a patient's ability to sense temperature variations. Referring to FIG. 11, temperature pads 414, 416 are aligned at a slight angle α of between about 10 degrees and about 20 degrees relative to end surface 420 such that temperature pads 414, 416 each extend in planes oblique to axis 412. This angle allows a single temperature pad 414 or temperature pad 416 to be placed against a patient's skin without the other temperature pad 416 or temperature pad 414 to engage the patient's skin. Each temperature pad 414, 416 is a Peltier device, similar to Peltier device 120 described above. Exemplary temperature pads 414, 416 can be Custom Thermoelectric 3111-5L31-03CFF3 PRX, Part Number PMC-40001-15-M. Temperature pads 414, 416 are controlled by thermoelectric coolers (not shown), such as the Murata NXFT15XH103FA2B025 PRX, Part Number PMC-40003.

Figure 17:
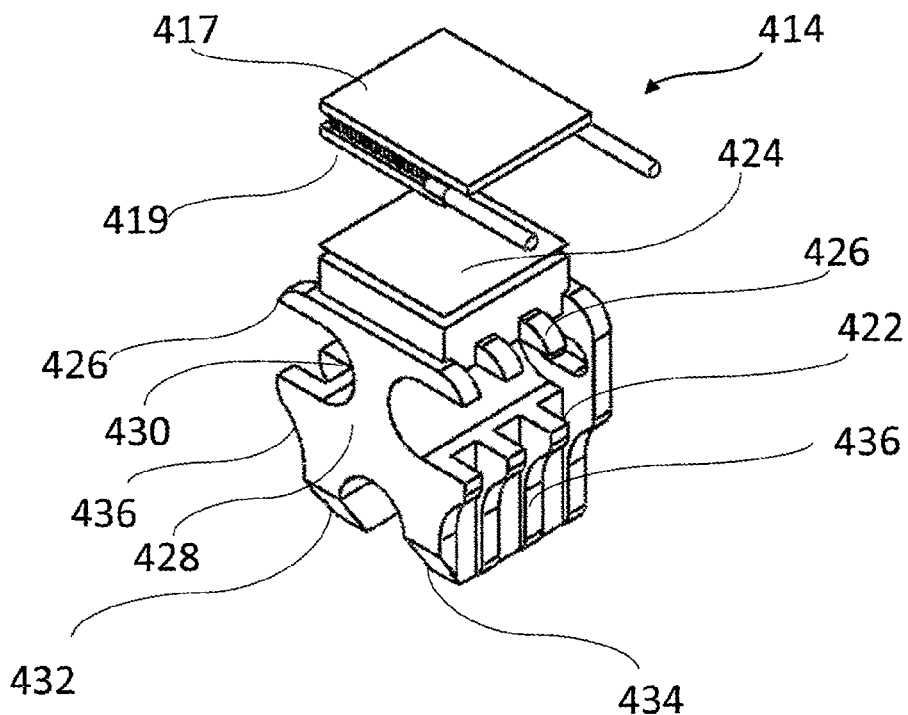
FIG. 17 is an exploded view of a heat sink used in the neuropathy detection device of FIG. 9.

As shown in FIG. 17, fixed temperature pad 414 includes an operating surface 417 that extends outwardly from head portion 404 and a heat sink surface 419 that extends inwardly, away from operating surface 417. Operating surface 417 is constructed from a ceramic material to isolate any electrical pathways to the patient when operating surface 417 is in contact with the patient.

Heat sink surface 419 is fixedly coupled to a heat sink 422 disposed in head portion 404. Heat sink 422 comprises a top surface 424 and a plurality of fins 426 extending outwardly from top surface 424. Top surface 424 is connected to a base portion 428 by a web 430. Base portion 428 is supported by a plurality of legs 432, 434. Each of legs 432, 434 has a plurality of fins 436 extending outwardly therefrom. Variable temperature pad 416 can be identical in construction to fixed temperature pad 414.

Figure 16:
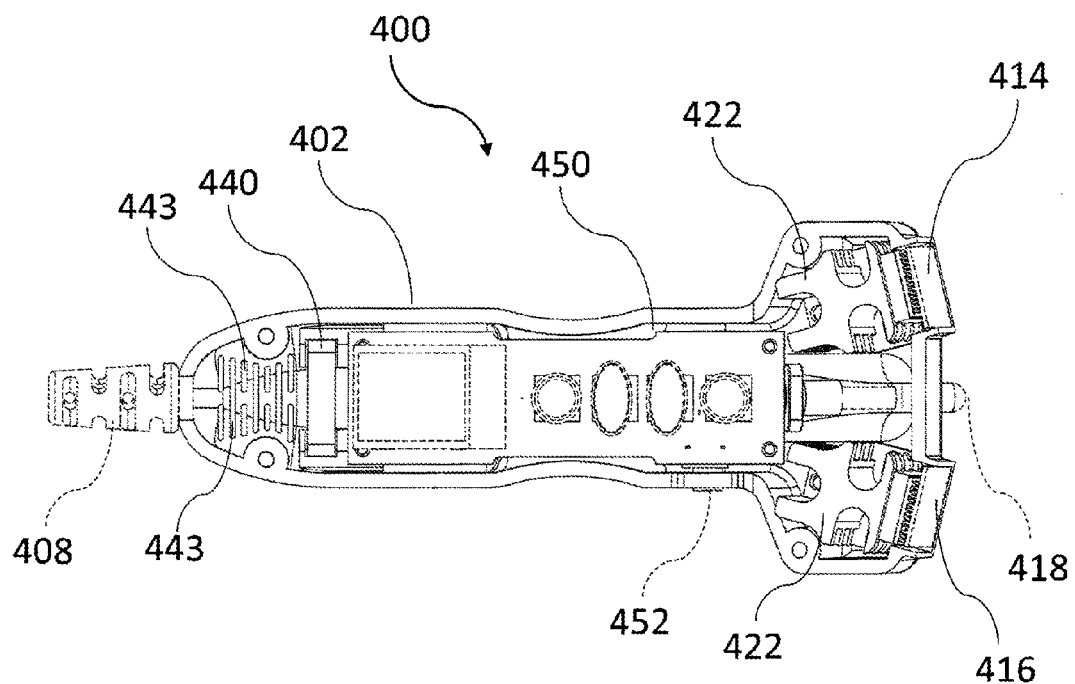
FIG. 16 is a sectional view of the neuropathy detection device of FIG. 9, taken along lines 16-16 of FIG. 12.

As shown in FIG. 16, a blower fan 440 is directed to blow air across heat sinks 422 to dissipate heat generated by temperature pads 414, 416. Blower fan 440 operates at all times when device 400 is in the temperature mode. An exemplary blower fan 440 can be a Sunon MC25060V2-000U-A99 PRZ, part number PMC-40004. Head portion 404 includes a plurality of vent openings 442 (shown in FIG. 14) formed therethough to provide for air circulation by blower fan 440. Vent openings 443 are located in handle portion 402 between blower fan 440 and cable connection 408. Vent openings 443 provide air blown by blower fan 440 over a controller 450 located in handle portion 402 and temperature surfaces 414, 416, located in head 404.

Fixed temperature surface 414 operates at about 25 degrees Celsius, and variable temperature surface 416 can vary in two degree increments between about 15 degrees Celsius and about 40 degrees Celsius.

A vibration tip, or probe, 418 is located along axis 412 generally between fixed temperature pad 414 and variable temperature pad 416. As shown FIG. 12, vibration tip 418 extends at an angle δ of between about 10 degrees and about 20 degrees relative to handle portion 402. Vibration probe 418 is operatively coupled to a linear resonance actuator 444 inside head portion 404. An exemplary linear resonance actuator 444 operates via a bipolar sine wave at a frequency of about 175 Hz and varying amplitude at a rated voltage of 2 volts RMS, with a typical operating current of about 69 mA RMS. An exemplary linear resonance actuator 444 can be a Precision Microdrives C10-100 PRX, Part Number PMC-40029. As the current to linear resonance actuator 444 decreases, the amplitude of vibration decreases. An exemplary maximum amplitude is about 1G, and vibration settings are reduced or increased in 0.2 degree increments for each of five (5) levels indicated by recuing current to linear resonance actuator 444.

Figure 18:
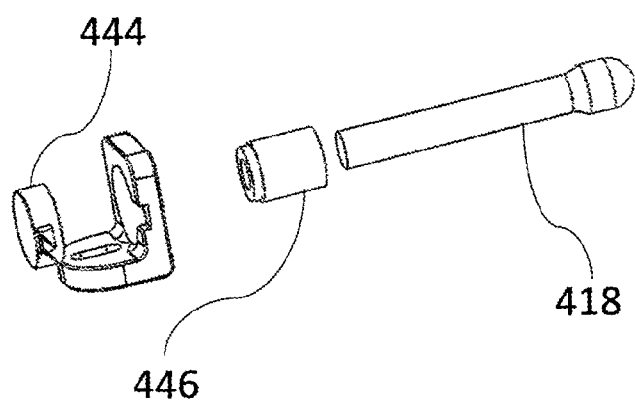
FIG. 18 is an exploded view of a vibration probe used in the neuropathy detection device of FIG. 9.

As shown in FIG. 18, a base 446 is attached to linear resonance actuator 444 so that vibration tip 418 can be mounted to base 446. In operation, no electrical pathways are transferred to the patient; the vibration is strictly a mechanical function.

Figure 12:
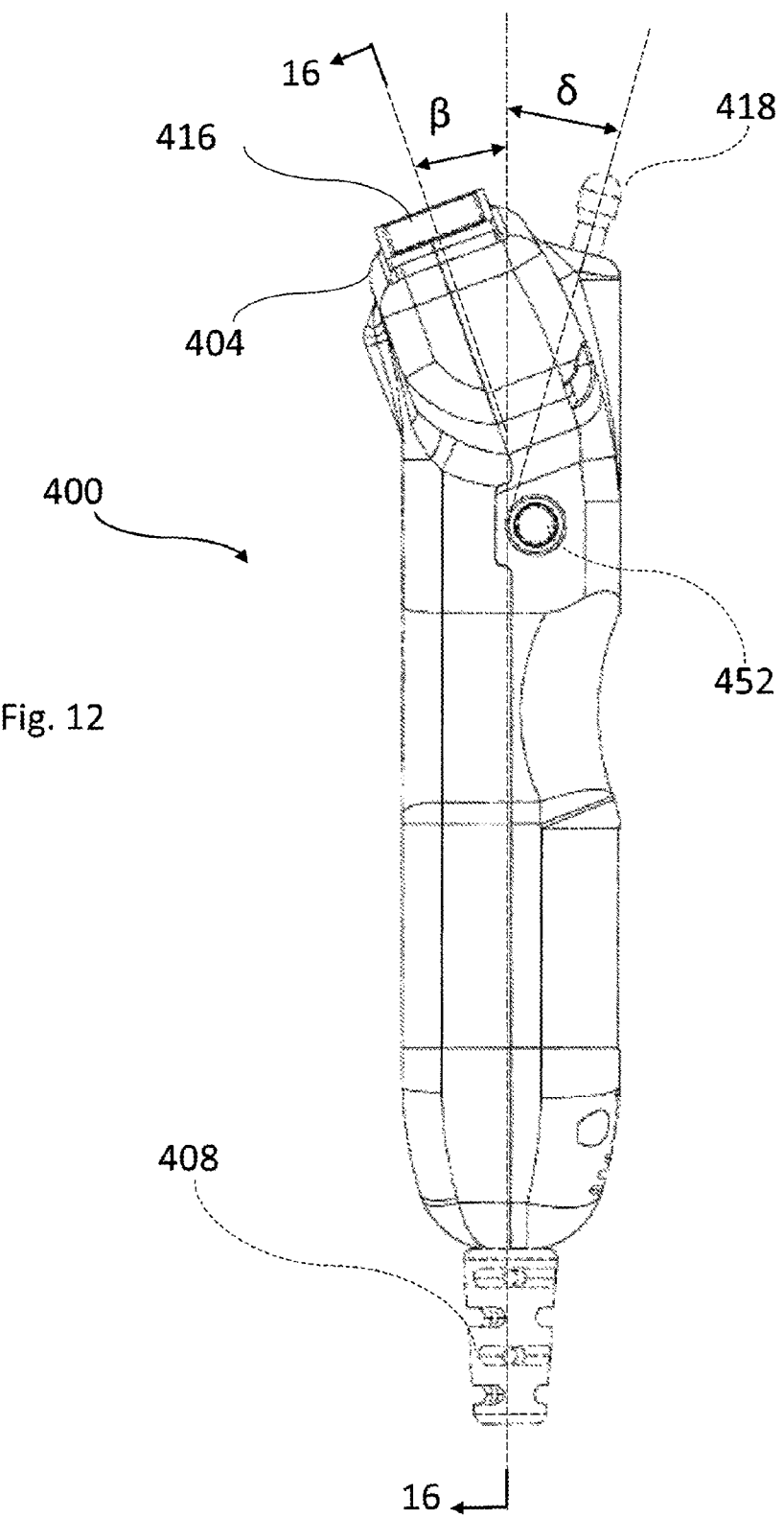
FIG. 12 is a right side view of the neuropathy detection device of FIG. 9.
Figure 13:
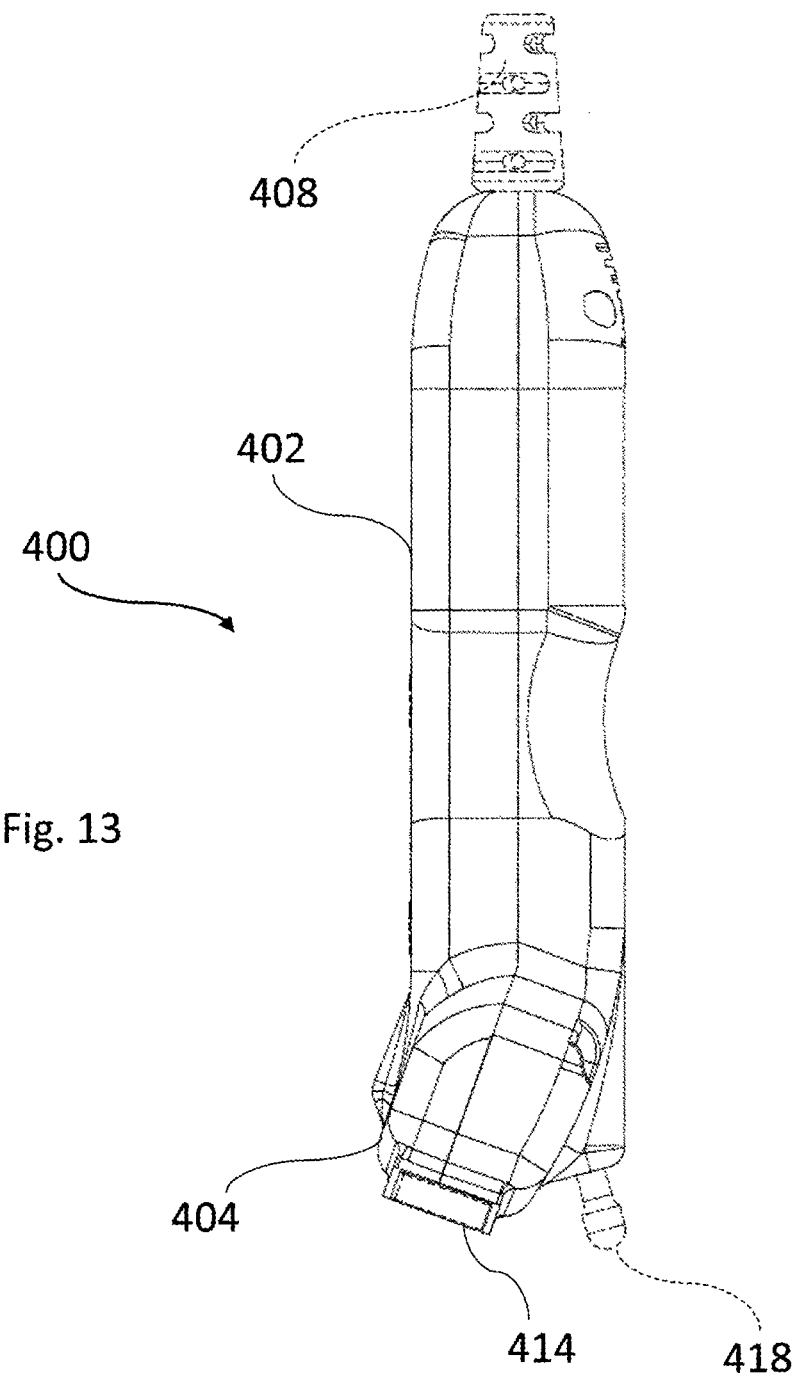
FIG. 13 is a left side view of the neuropathy detection device of FIG. 9.
Figure 14:
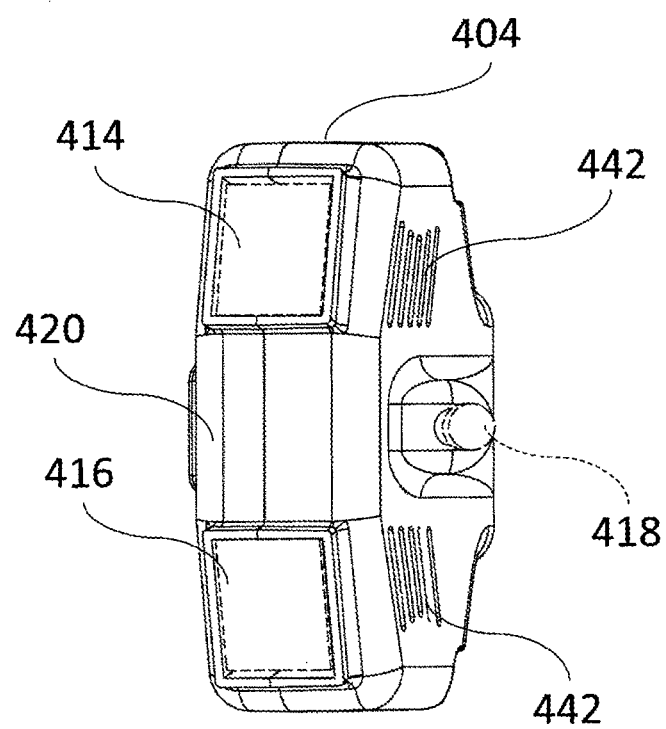
FIG. 14 is a top view of the neuropathy detection device of FIG. 9.
Figure 15:
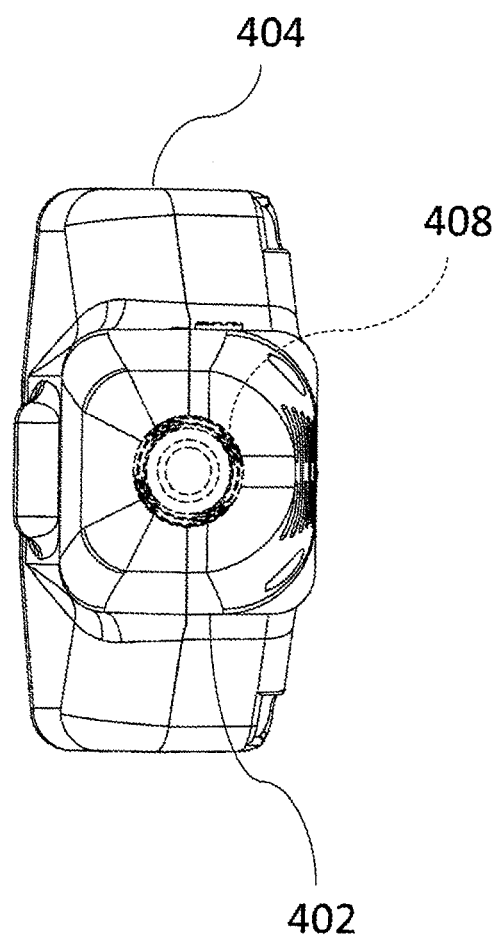
FIG. 15 is a bottom view of the neuropathy detection device of FIG. 9.

Referring to FIG. 12, handle portion 402 contains a controller 450 that is used to control device 400. Controller 450 can be a microcontroller or other suitable electronic controller. Fixed temperature surface 414, variable temperature surface 416, and vibration probe 418 are all operatively coupled to controller 450. Vibration probe 418 is operatively coupled to controller 450 via linear resonance actuator 444, which is operatively coupled to controller 450. Controller 450 sets each of fixed temperature surface 414 and variable temperature surface 416 at desired temperatures at a rate of temperature change of not less than 1° C. per second. Controller 450 is adapted to control only one of temperature surfaces 414, 416 and vibration tip 418 at one time.

Controller 450 can include exemplary software written in "C" programming language written for an Arduino board, although those skilled in the art will recognize that other programming languages can be used.

Device 400 includes a plurality of buttons that are operatively connected to controller 450 and are used to operate device 400. Buttons include a power button 452 that is used to turn device 400 ion and off. As shown in FIG. 12, power button 452 is located on handle portion 402, proximate to head portion 404. The location of power button 452 allows a user to grasp handle portion 402 with his/her fingers and operate power button 452 with his/her thumb.

Figure 10:
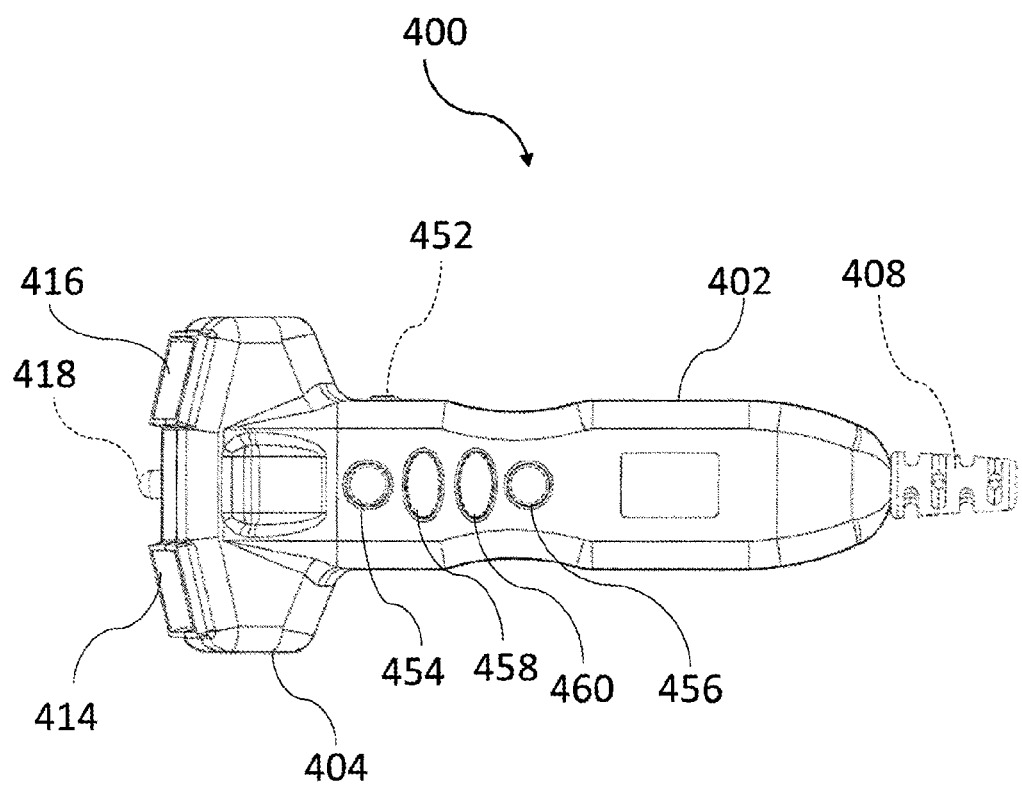
FIG. 10 is a front view of the neuropathy detection device of FIG. 9.

Referring to FIG. 10, device 400 also includes a temperature selection button 454 that, when pressed, puts device 400 into temperature mode and transmits a signal to controller 450 to operate fixed temperature surface 414 and variable temperature surface 416. Device 400 also includes a vibrator selection button 456 that, when pressed, puts device 400 into vibration mode and transmits a signal to controller 450 to operate vibration probe 418. Device 400 can only be in one of temperature mode and vibration mode at any one time. The user switches between temperature mode and vibration mode by selecting either temperature selection button 454 or vibrator selector button 456.

Device 400 also includes an up button 458 that, when device 400 is in temperature mode, increases the temperature of variable temperature surface 416 in increments of 1 degree Celsius each time up button 458 is pressed and, when in vibration mode, increases the vibration amplitude of vibration probe 418 in increments of about 20% total vibration amplitude each time up button is pressed. Device 400 further includes a down button 460 that, when device 400 is in temperature mode, decreases the temperature of variable temperature surface 416 in increments of 2 degree Celsius each time down button 460 is pressed and, when in vibration mode, decreases the vibration amplitude of vibration probe 418 in increments of about 20% total vibration amplitude each time down button 460 is pressed.

Controller 450 is configured to turn device 400 to an "off" condition after a predetermined time period of none of the plurality of control buttons 452, 454, 456, 458, 460 are activated. In an exemplary embodiment, the time period may be 120 seconds±10 seconds.

Figure 19:
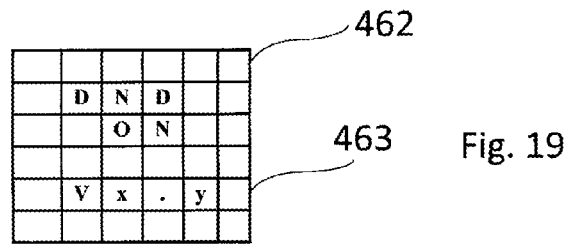
FIG. 19 shows an exemplary screen display upon start-up of the neuropathy detection device of FIG. 9.

As shown in FIG. 10, handle portion 402 further includes a visual display 462 electronically and operatively coupled to controller 450 to display one of a select mode, a temperature mode, and a vibration mode. An exemplary visual display 462 that can be used with device 400 is a Crystalfontz CFA04265A-TTL PRX Part Number PMC-40036. On start-up of device 400, as shown in FIG. 19, during which time all electronics, peripherals, and software variables are initialized, visual display 462 displays an exemplary message 463 of "DND ON Vx·y" for about three seconds.

Figure 20:
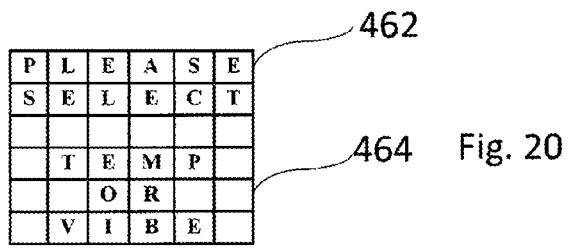
FIG. 20 shows an exemplary screen display for mode selection of the neuropathy detection device of FIG. 9.
Figure 21:
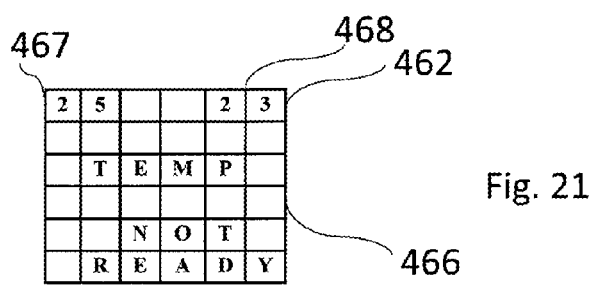
FIG. 21 shows an exemplary screen display when temperature mode is selected for the neuropathy detection device of FIG. 9.

After device 400 has been started, visual display 462 provides a prompt 464, shown in FIG. 20, for the user to select either temperature mode or vibration mode. When the user selects temperature mode, visual display 462 changes to display 466, shown in FIG. 21, which displays that the temperature mode has been selected, and also displays the temperature 467 of fixed temperature surface 414 and the temperature 468 of variable temperature surface 416. Additionally, until temperature surfaces 414, 416 reached their selected temperatures, a "TEMP NOT READY" message is displayed on visual display 462. When both temperature surfaces 414, 416 reach their selected temperatures, a "TEMP READY" message is displayed on visual display 462.

Figure 22:
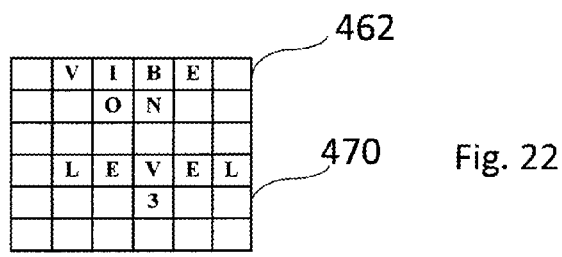
FIG. 22 shows an exemplary screen display when vibration mode is selected for the neuropathy detection device of FIG. 9.
Figure 23:
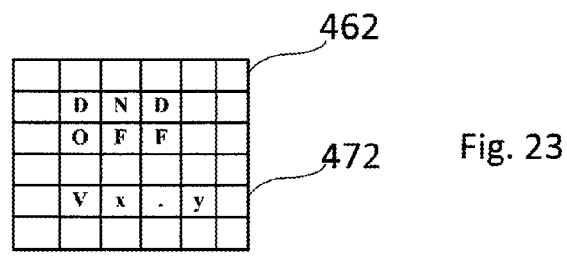
FIG. 23 an exemplary screen display in shut down mode for the neuropathy detection device of FIG. 9.

When the user selects vibration mode, visual display 462 changes to display 470, shown in FIG. 22, which indicates that the vibration mode has been selected and displays the vibration level of vibration probe 418. When the user presses power button 452 to shut down device 40, visual display 462 changes to display 472, which displays an exemplary message of "DND OFF Vx·y" for about three seconds.

An exemplary method of using any of devices 100, 200, 300, 400 will now be described, with device 400 being used as an exemplary device representative of devices 100, 200, 300 as well.

Device 400 may be used to provide an objective method for screening a patient for neuropathy. Particularly, device 400 may be used for screening a patient's feet for neuropathy. Such screening results can lead a physician to diagnose whether or not a patient may be suffering from a particular medical condition.

In an exemplary method, to use device 400, the user turns on device 400 by pressing power button 452. While device 400 is powering up, visual display 462 shows screen 463, shown in FIG. 19. After device 400 is fully powered, visual display 462 changes to screen 464, shown in FIG. 20. The user then determines whether to enter temperature mode or vibration mode, and presses temperature button 454 or vibration button 456 to pick the desired mode.

The temperature settings for each of fixed temperature surface 414 and variable temperature surface 416 are shown as temperatures 467, 468, respectively. Until the temperatures of fixed temperature surface 414 and variable temperature surface 416 reach their pre-set temperatures, the "NOT READY" indication is displayed on visual display 462. In an exemplary embodiment, the pre-set temperatures are 25 degrees Celsius for fixed temperature surface 414 and 23 degrees Celsius for variable temperature surface 416.

The temperature of variable temperature surface 416 can be adjusted upward by an amount of 2 degrees Celsius at a time by pressing up button 458 until the desired variable temperature is selected. When visual display 462 displays the "TEMP READY" message, the user alternates placing fixed temperature surface 414 and variable temperature surface 416 to a region of interest on a patient, such as, for example, the bottom of the patient's foot, and determines whether the patient can discriminate between the two temperature settings. If the patient cannot discriminate between the two temperatures, the user presses either up button 458 or down button 460 to increase the delta temperature between fixed temperature surface 414 and variable temperature surface 416 and the process of touching fixed temperature surface 414 and variable temperature surface 416 to the region of interest on the patient is repeated.

If variable temperature surface 416 is adjusted to a temperature less than fixed temperature surface, in an exemplary embodiment, the maximum delta temperature is about 10 degrees Celsius. If variable temperature surface 416 is adjusted to a temperature greater than fixed temperature surface, in an exemplary embodiment, the maximum delta temperature is about 15 degrees Celsius. Those skilled in the art, however, will recognize that the delta temperatures can be as much as 20 degrees Celsius. Variable temperature surface 416 can be reset to their pre-set temperatures by pressing vibration button 456 and then pressing temperature button 454.

If the user presses vibration button 456, device 400 goes into vibration mode. The vibration level of vibrator tip 418 is pre-set to its lowest level, level 1. The user touches a location on the patient's foot with vibration tip 418 for a period of time, such as, for example, two seconds. The user then determines whether the patient can sense the vibration. Depending on the patient's response, the user can press either up button 458 to increase the vibration amplitude or down button 460 to decrease the vibration amplitude and touch vibration tip 418 to the patient's foot in the same area, and the process is repeated. The vibration amplitude of vibration tip 418 can be reset to its pre-set vibration amplitude by pressing temperature button 454 and then pressing vibration button 456.

When the user has concluded screening the patient with device 400, the user can turn device 400 of by pressing power button 452. Alternatively, if none of buttons 452-460 are pressed for a predetermined period of time, such as, for example, 120 seconds, controller 450 automatically shuts off device 400.

Although the invention is illustrated and described herein with reference to specific embodiments, the invention is not intended to be limited to the details shown. Rather, various modifications may be made in the details within the scope and range of equivalents of the claims and without departing from the invention. For example, the inventive device may include three or more temperature surfaces. Alternatively, or in addition, the inventive device may include two or more vibration surfaces, each capable of operating at different amplitudes and/or frequencies, or with different geometries to vary the amount of surface area in contact with the patient.

What is claimed:
1. A hand-held neuroscreening device comprising:
   an elongate handle having:
      a first end;
      a second end;
      a fan located in the first end;
      a first vent opening located proximate to the fan; and
      a longitudinal axis extending therethrough between the first end and the second end; and
   a head portion fixedly attached to the first end of the handle, the head portion having a longitudinal axis, the head portion having:
      a second vent opening;
      a fixed temperature surface extending in a first plane oblique to the head portion longitudinal axis;
      a variable temperature surface extending in a second plane oblique to the first plane; and a vibration probe extending outwardly from the head portion, away from the body, between the fixed temperature surface and the variable temperature surface.

2. The hand-held neuroscreening device according to claim 1, wherein the head portion longitudinal axis extends obliquely relative to the longitudinal axis of the body.

3. The hand-held neuroscreening device according to claim 1, further comprising an end surface extending between the fixed temperature surface and the variable temperature surface, the end surface being parallel to the longitudinal axis of the handle.

4. A method of screening for neuropathy, comprising the steps of:
   (a) using the device according to claim 1, selecting between operating the fixed and variable temperature surfaces and the vibration probe;
   (b) touching a location on a patient with the device; and
   (c1) determining whether the patient is able to discriminate between temperature differences between the fixed temperature pad and the variable temperature pad if the step of operating the fixed and variable temperature surfaces was selected; and
   (c2) determining whether the patient is able to discriminate vibrations if the step of operating the vibration probe was selected.

5. The method according to claim 4, further comprising, in step (b), if the step of operating the fixed and variable temperature surfaces was selected, touching the fixed temperature pad to the location and then touching the variable temperature pad to the location.

6. The method according to claim 5, further comprising, if the patient is not able to discriminate between the temperature differences in step (c1), increasing the temperature difference and repeating step (b).

7. The method according to claim 4, further comprising, in step (b), if the step of operating the vibration probe was selected and the patient is not able to discriminate vibrations in step (c2), increasing the vibration amplitude and repeating step (b).

8. A method of screening for neuropathy in a patient, the method comprising the steps of:
   (a) using a single hand-held device, touching the patient in a location with a first temperature pad, the first temperature pad being electronically held at a fixed temperature;
   (b) using the single hand-held device, touching the patient in the location with a second temperature pad, the second temperature pad being held electronically at a variable temperature, wherein the variable temperature is less than the fixed temperature and wherein a maximum difference between the fixed temperature and the variable temperature is about 20 degrees Celsius;
   (c) determining whether the patient can distinguish between the fixed temperature and the variable temperature and, if the patient cannot distinguish between the fixed temperature and the variable temperature, changing the variable temperature and repeating steps (a)-(c) until the patient can distinguish between the fixed temperature and the variable temperature; and
   (d) using the single hand-held device, touching the patient in the location with vibration probe, the vibration probe being located between the first temperature pad and the second temperature pad; and
   (e) determining whether the patient senses vibrations from the vibration probe.

9. The method according to claim 8, wherein the variable temperature has a maximum temperature is greater than the fixed temperature.

10. The method according to claim 8, further comprising, prior to step (a), the step of selecting on the device a temperature mode from an option of the temperature mode and a vibration mode.

11. The method according to claim 10, further comprising:
    after step (c), leaving the temperature mode and entering the vibration mode.

12. The method according to claim 11, further comprising, if the patient cannot sense the vibrations, pressing a first button to increase the vibrational frequency of the vibration probe.

13. The method according to claim 11, further comprising, viewing an indication on a viewing screen that the vibration mode has been selected.

14. The method according to claim 10, further comprising viewing an indication on a viewing screen that the temperature mode has been selected.

15. The method according to claim 14, further comprising the step of displaying the temperature of each of the first temperature pad and the second temperature pad on the viewing screen.

16. The method according to claim 10, wherein, when the temperature mode has been selected, the fixed temperature pad is regulated to the fixed temperature and the variable temperature is regulated to the variable temperature, less than the fixed temperature.

17. A hand-held neuroscreening device comprising:
    an elongate handle having:
       a first end;
       a second end;
       a temperature selection button;
       a vibration selection button;
       an up button; and
       a down button;
    and
    a head portion fixedly attached to the first end of the handle, the head portion having:
       a vibration probe operatively connected to the vibration selection button and to the up and down buttons;
       a fixed temperature surface operatively connected to the temperature selection button, the fixed temperature surface being located on a first side of the vibration probe; and
       a variable temperature surface operatively connected to the temperature selection button and to the up and down buttons, the variable temperature surface being located on a second side of the vibration probe away from the fixed temperature surface.

18. The hand-held neuroscreening device according to claim 17, wherein the handle further comprises a display screen adapted to display one of a select mode, a temperature mode, and a vibration mode.

* * * * *